(12) United States Patent
Watzlawik

(10) Patent No.: US 10,307,327 B1
(45) Date of Patent: Jun. 4, 2019

(54) JELQ DEVICE

(71) Applicant: Hernan Watzlawik, Huntington Park, CA (US)

(72) Inventor: Hernan Watzlawik, Huntington Park, CA (US)

( * ) Notice: Subject to any disclaimer, the term of this patent is extended or adjusted under 35 U.S.C. 154(b) by 0 days.

(21) Appl. No.: 16/195,884

(22) Filed: Nov. 20, 2018

(51) Int. Cl.
*A61F 5/00* (2006.01)
*A61H 19/00* (2006.01)
*A61F 5/41* (2006.01)

(52) U.S. Cl.
CPC ............... *A61H 19/32* (2013.01); *A61F 5/41* (2013.01); *A61F 2005/414* (2013.01); *A61H 2201/0153* (2013.01); *A61H 2201/1253* (2013.01)

(58) Field of Classification Search
CPC ........... A61H 19/00; A61H 19/32; A61F 5/41; A61F 2005/411; A61F 2006/047
USPC ...................................................... 600/38–41
See application file for complete search history.

(56) References Cited

U.S. PATENT DOCUMENTS

| 9,907,724 B2 * | 3/2018 | Mercado Diaz | A61H 19/32 |
| 2013/0226045 A1 * | 8/2013 | Li | A61F 5/41 601/18 |

* cited by examiner

*Primary Examiner* — John P Lacyk

(57) ABSTRACT

An ergonomic and two-hands operated device for exercising a male genital organ is disclosed. The device comprises a fixed member and a movable member. The device further includes a first mounting bracket and a second mounting bracket arranged to provide structural support for maintaining a spaced parallel relationship between the fixed member and the movable member. The device further includes a pair of handles to control the open and closing of the device. The device further includes squeezing means arranged to symmetrically compress and adapt to fit the shape of the male genital organ in a centered position. The squeezing means is adapted to provide a sealed grip around the male genital organ free of pinch points.

16 Claims, 8 Drawing Sheets

JELQ DEVICE

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to an apparatus for exercising the male genital organ, and more particularly to an apparatus that can be adapted for increasing the size of the male genital organ.

DISCUSSION OF RELATED ART

Various techniques have been utilized for increasing the size of the male genital organ. Jelquing, which utilizes the principles of the ancient Arabic technique of Jelq, is a popular male member enhancement exercise practiced by men all over the world. These techniques increase the flow of blood into the male genital organ and provide a safe way to enlarge the male member for improved erection. Moreover, these exercises are free from risks caused by the side effects of medication.

One prior art device for assisting such an exercise is disclosed in U.S. Pat. Appl. No. 20130226045 by Li Hui on Aug. 29, 2013 that describes a penis enlargement exercising system including a penis enlargement exerciser, a penis protecting cover, a heating device, and a pubic hair separating plate. However, this penis enlargement exerciser includes a penis protector cover disposed around the penis for protecting the skin from being pushed into a gap between the slider and the frame thereby providing a complex structural arrangement. Moreover, this device includes a complex arrangement of the handles which may be difficult to control during exercise by the user.

Publication Number CN106619021 issued to Liu Baobin on May 10, 2017 discloses a penis enlargement massage trainer comprising a clamping device, an opening and closing frame and a moving and adjusting device. However, this massage trainer includes a moving and adjusting device providing a complex structural arrangement that fails to provide flexibility and comfort.

U.S. Pat. No. 9,907,724 issued to Mercado Diaz on Mar. 6, 2018 discloses a device that stimulates and aids penis jelqing, or penis milking massage. However, this device includes a scissors-like structural arrangement that fails to maintain the male genital centered position and fails to provide symmetrical compression around of the male genital organ which may be uncomfortable for the user. Moreover, this device includes a complex arrangement of the handles which may be difficult to control during the jelqing motion by the user.

Therefore, there is a need for an improved apparatus for exercising the male genital organ that would be designed substantially free of pinch points to prevent the skin from being caught or injured between moving parts during the exercise. Such an apparatus would be adapted to provide flexibility and comfort. As such the squeezing means utilized in the above-mentioned prior arts would be designed to keep the male genital organ in a centered position and would be adapted to symmetrically compress the male genital organ. However, the handles utilized in the above-mentioned prior arts would be designed to be operated in a relatively simple manner and would be adapted to facilitate an appropriate ergonomic positioning of the user's hands. Moreover, such an apparatus would eliminate the existing structural complexities of other inventions and be sufficiently flexible to provide ease of desired positioning. The present invention accomplishes these objectives.

SUMMARY OF THE INVENTION

The present invention is an ergonomic and two-hand operated device for exercising a male genital organ comprising a fixed member having a first cylindrical mounting portion, a V-shaped portion, a second cylindrical mounting portion and a lever end. The device further comprises a movable member having a first cylindrical mounting portion, a V-shaped portion, a second cylindrical mounting portion and a lever end. The V-shaped portion of the fixed member and the V-shaped portion of the movable member each may include an outward curved shape.

The device further comprises a first mounting bracket having a through hole and a blind hole arranged in parallel. The device further comprises a second mounting bracket having a blind hole and a through hole arranged in parallel. The first mounting bracket and the second mounting bracket arranged to provide structural support for maintaining a spaced parallel relationship between the fixed member and the movable member.

The first cylindrical mounting portion and the second cylindrical mounting portion of the fixed member are securely attached, respectively, within the blind hole of the second mounting bracket and within the through hole of the first mounting bracket by way of a plurality of spring pins. The first cylindrical mounting portion and the second cylindrical mounting portion of the movable member are pivotally engaged, respectively, within the blind hole of the first mounting bracket and within the through hole of the second mounting bracket.

As configured, the movable member enjoys pivotal movement in relation to the mounting bracket, the fixed member enjoys radial movement in relation to the movable member.

The device further includes a pair of handles, each handle is securely attached, respectively, to the lever end of the fixed member and to the lever end of the movable member. The handles operate the open and closed position of the device. As configured, the handles are adapted to facilitate an appropriate ergonomic positioning of a user's hands during exercise The device further comprises squeezing means, arranged to symmetrically compress and adapt to fit the shape of the male genital organ. The squeezing means includes a first silicone sleeve having a pair of end portions and a second silicone sleeve having a pair of end portions. The first silicone sleeve is mounted on the V-shaped portion of the fixed member and the second silicone sleeve is mounted on the V-shaped portion of the movable member. The pair of end portions of the first silicone sleeve arranged to be held in frictional contact with the pair of end portions of the second silicone sleeve, to ensure a sealed squeezing means around the male genital organ.

The blind hole and the through hole of the first and the second mounting brackets each may include a counterbored section for overlapping the end portions of the first and the second silicone sleeves.

As configured, the squeezing means is adapted to ensure the central positioning of the male genital organ during the exercise.

The device, as configured, is substantially free of pinch points to prevent the skin from being caught or injured between moving parts during the exercise.

In use, before initiating the process, the male genital organ needs to be warmed up; approximately of about 60% erect and lubricated. The device is configured herein to be operated with the device parallel to the waist line in the open position, and the male genital organ can be inserted into the device. The pair of handles may be rotated in opposite directions relative to each other in order to adapt the squeezing means to compress the base of the male genital organ. The device may be slowly pulled along the shaft of the male genital organ to force the blood towards the head of the male genital organ. The device is placed near the head of the male genital organ and holding the device for approximately of about 2 seconds. The handles can be rotated in an inverse direction to open the squeezing means for repositioning the device to the base of the male genital organ.

The present invention facilitates the exercising of the male genital organ with the improved device designed substantially free of pinch points. Such an apparatus is adapted to provide flexibility and comfort. Moreover, such an apparatus eliminates the existing structural complexities of other inventions and is sufficiently flexible to provide ease of desired positioning. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Figure 1:
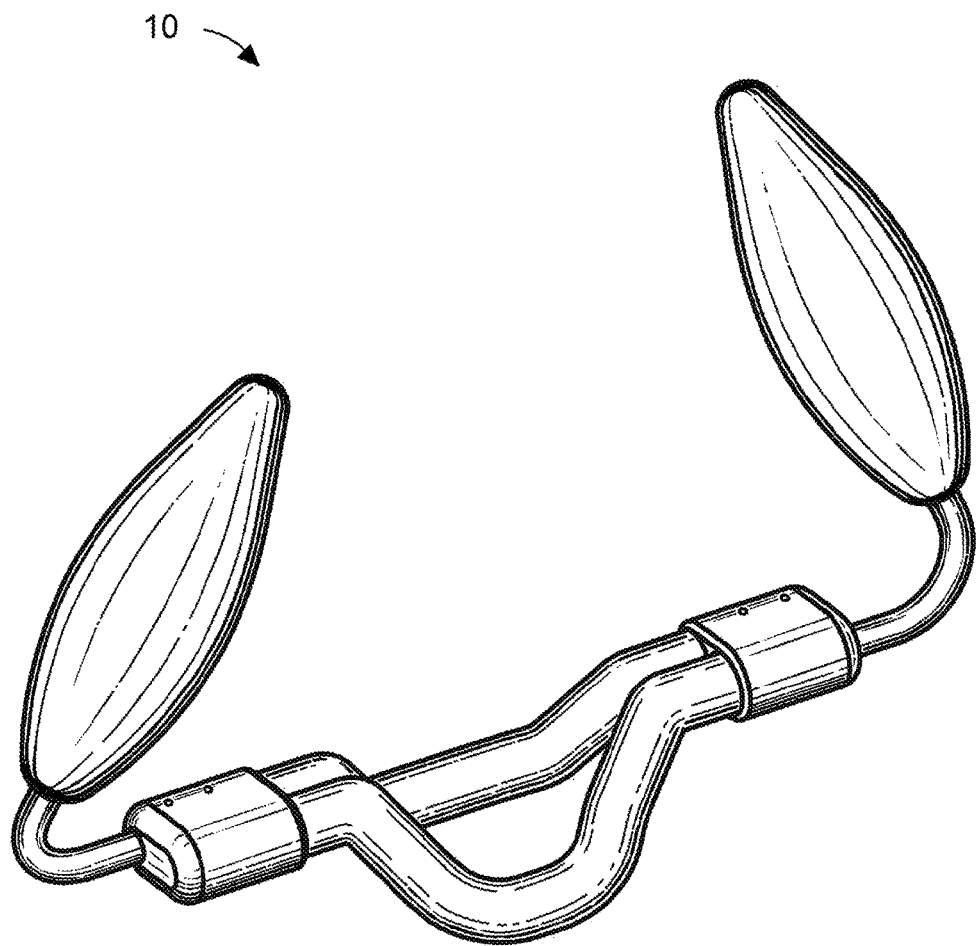
FIG. 1 is a perspective view of a preferred embodiment in accordance with the present invention in the open position, for exercising a male genital organ.

FIG. 1 is a perspective view of an ergonomic and two-hand operated device 10 for exercising a male genital organ in the open position.

Figure 2:
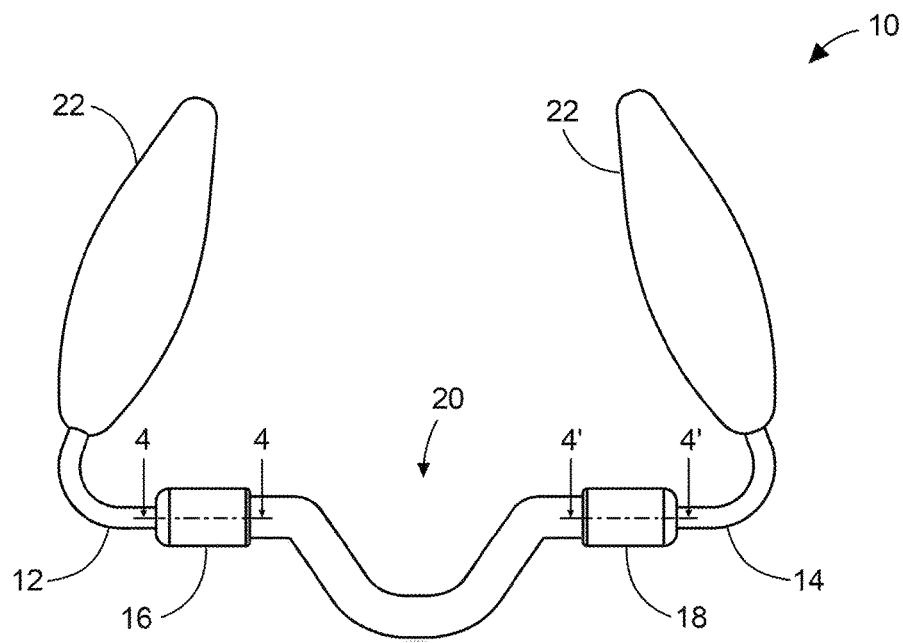
FIG. 2 is a front elevational view of the preferred embodiment in accordance with the present invention in the closed position, for exercising a male genital organ.

FIG. 2 is a front elevational view of the preferred embodiment in accordance with the present invention illustrating the device 10 in the closed position, comprising a fixed member 12 a movable member 14 a first mounting bracket 16 a second mounting bracket 18 squeezer means 20 and a pair of handles 22. The longitudinal axis of the handles 22 may lie at an inward angle from horizontal of approximately 75 degrees. The handles operate the open and closed position of the device.

Figure 3:
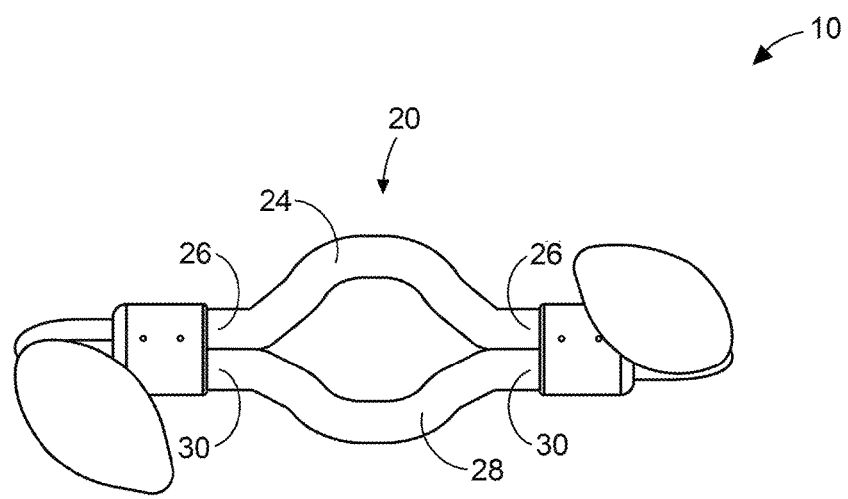
FIG. 3 is a top view of the of the preferred embodiment in accordance with the present invention in the open position.

FIG. 3 is a top view of the present invention illustrating the device 10 in the open position, showing the squeezer means 20, arranged to symmetrically compress and adapt to fit the shape of the male genital organ. The squeezing means 20 comprising a first silicone sleeve 24 having a pair of end portions 26. The squeezing means 18 further comprises a second silicone sleeve 28 having a pair of end portions 30. As configured, the pair end portions 26 of the first silicone sleeve 24 arranged to maintain frictional contact with the pair of end portions 30 of the second silicone sleeve 28 to ensure a sealed squeezing means around the male genital organ. Each silicone sleeve 24, 28 may be made of a tubular piece of medical grade silicone having a durometer of about 35 to about 50 when measured on the Shore A scale. The squeezing means 20 is adapted to ensure the central positioning of the male genital organ during use.

Figure 4:
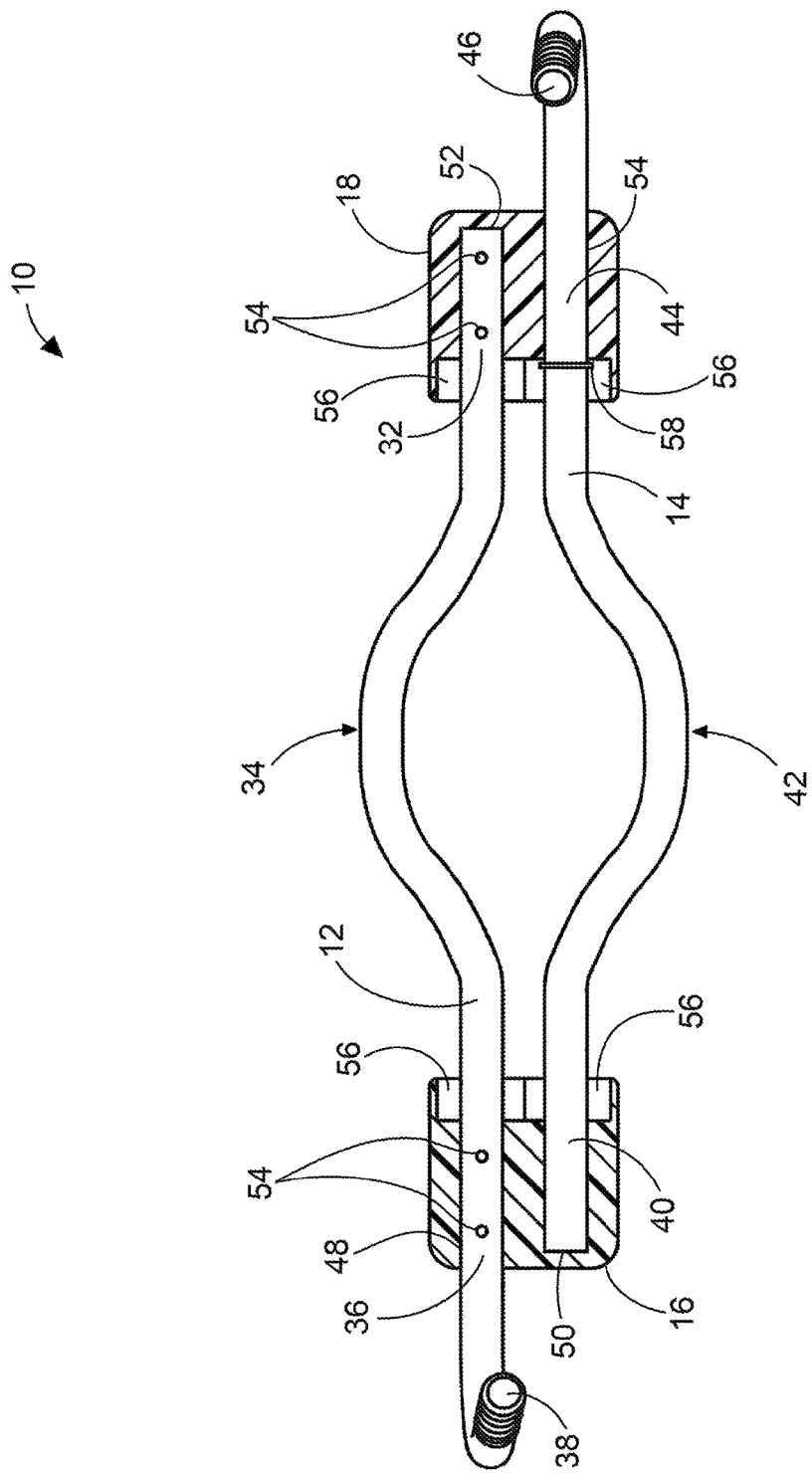
FIG. 4 is a top view of the of the preferred embodiment in accordance with the present invention in a partially open position, showing the device with the squeezing means and handles being removed for clarity, with the drawing being partially sectioned, taken along lines 4-4 and 4'-4' of FIG. 2, to illustrate the working elements of the embodiment.

FIG. 4 is a top view of the of the preferred embodiment in accordance with the present invention, showing the device 10 in a partially open position with the squeezing means and handles being removed for clarity, with the drawing being partially sectioned, taken along lines 4-4 and 4'-4' of FIG. 2, to illustrate the working elements of the embodiment. The fixed member 12 comprises a first cylindrical mounting portion 32 a V-shaped portion 34 a second cylindrical mounting portion 36 and a lever end 38. The movable member 14 comprises a first cylindrical mounting portion 40 a V-shaped portion 42 a second cylindrical mounting portion 44 and a lever end 46.

The first mounting bracket 16 comprises a through hole 48 and a blind hole 50, arranged in parallel. The second mounting bracket 18 comprises a blind hole 52 and a through hole 54, arranged in parallel. The first mounting bracket 16 and second mounting bracket 18 arranged to provide a structural support for maintaining a spaced parallel relationship between the fixed member 12 and the movable member 14. As configured, the first cylindrical mounting portion 32 and second cylindrical mounting portion 36 of the fixed member 12 are securely attached, respectively, within the blind hole 52 of the second mounting bracket 18 and within the through hole 48 of the first mounting bracket 16 by way of a plurality of spring pins 54. The first cylindrical mounting portion 40 and the second cylindrical mounting portion 44 of the movable member 14 are pivotally engaged, respectively, within the blind hole 50 of the first mounting bracket 16 and within the through hole 54 of the second mounting bracket 18. The blind holes 52, 50 and through holes 48, 54 each may include a counterbored section 56 for overlapping the end portions of the silicone sleeves (not illustrated for clarity purposes).

As configured, the fixed member 12 enjoys radial movement in relation to the movable member 14, and the movable member 14 enjoys pivotal movement in relation to the mounting brackets 16, 18. The movable member 14 may include a retaining clip 58 arranged to maintain the alignment between the V-shaped portions 34,42. The fixed member 12 and the movable member 14 may be made from a formed metal rod.

Figure 5:
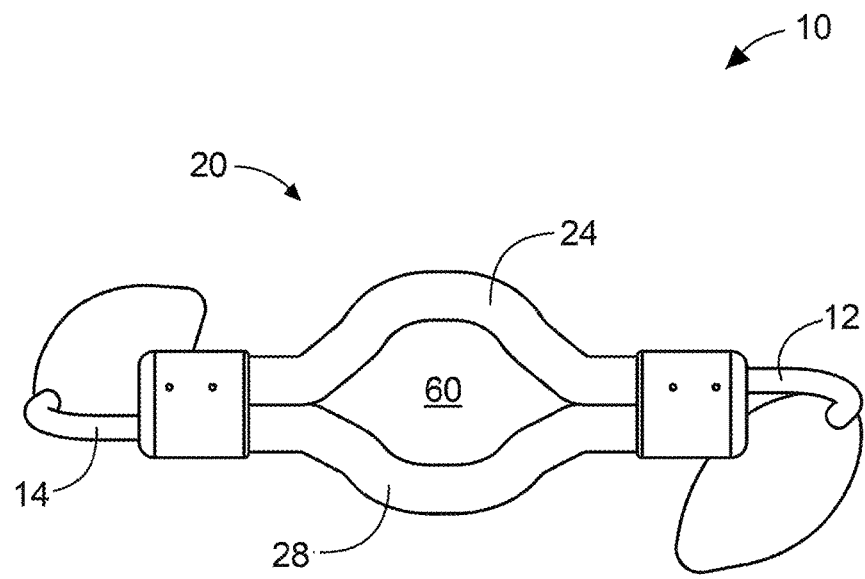
FIG. 5 is a bottom view of the present invention in the open position.

FIG. 5 is a bottom view of the present invention illustrating the device 10 in the open position, showing the first silicone sleeve 24 mounted on the V-shaped portion (not shown) of the fixed member 12 and the second silicone sleeve 28 mounted on the V-shaped portion (not shown) of the movable member 14. The squeezing means 20, defines a substantially symmetrical cavity 60 for receiving and compressing the male genital organ, with the approximate dimensions of 2.5 inches wide and 1.5 inches of length. As configured, the device 10 is substantially free of pinch points to prevent the skin from being caught or injured between moving parts during the exercise.

Figure 6:
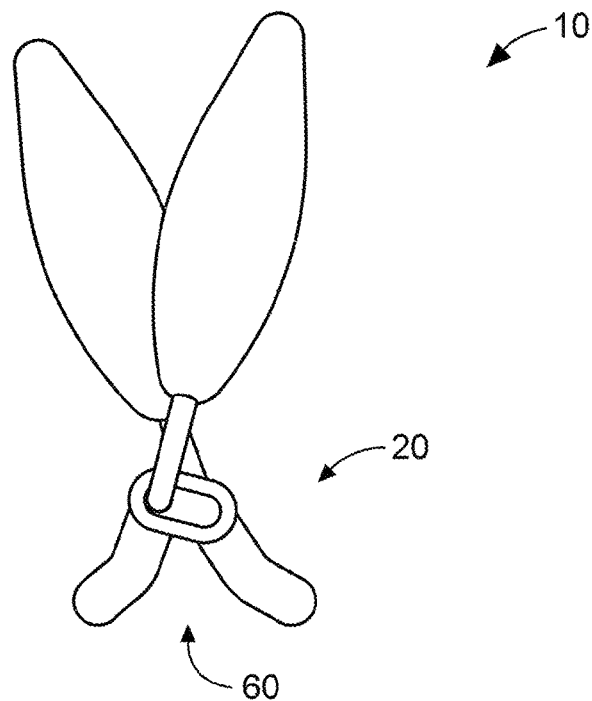
FIG. 6 is a side elevational view of the preferred embodiment in accordance with the present invention in the open position.

FIG. 6 is a side view of the present invention illustrating the device 10 in the open position, showing the substantially symmetrical cavity 60 of the squeezing means 20 for introducing and compressing the male genital organ.

Figure 7A:
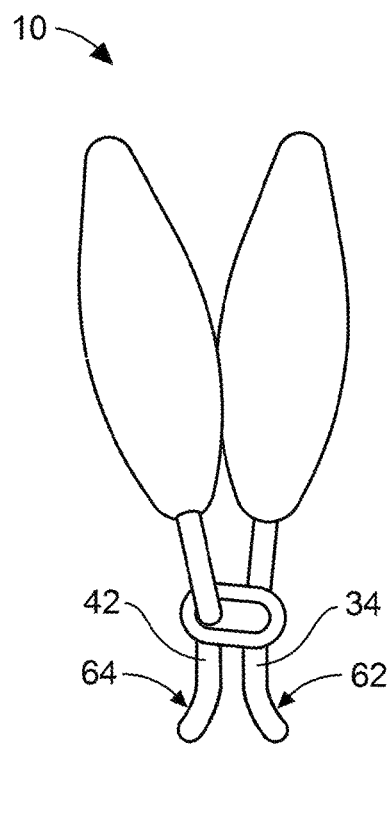
FIG. 7a is a side elevational view of the preferred embodiment in accordance with the present invention in the closed position with the squeezing means removed for clarity.

FIG. 7a is a side elevational view of the present invention illustrating the device 10 in the closed position, with the squeezing means (not shown) removed for clarity, showing the V-shaped portion 34 and the V-shaped portion 42. The V-shaped portions 34 and 42 each may include, respectively, an outward curved shape 62 and 64. The outward curved shapes 62, 64 are designed to create a cavity (not shown), that is further described below with reference to FIGS. 7b and 8.

Figure 7B:
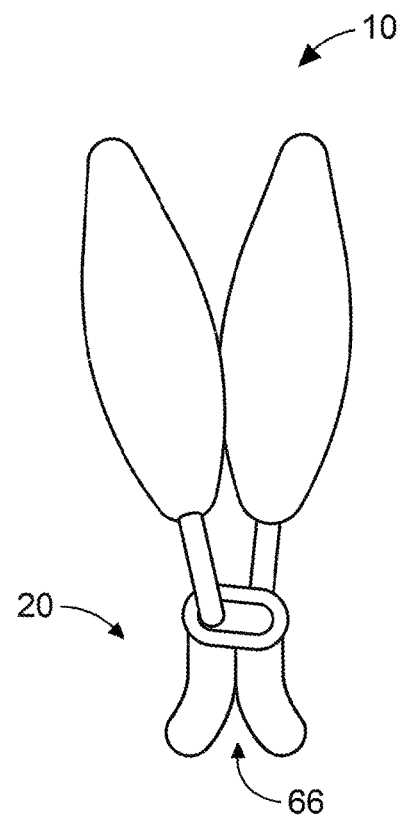
FIG. 7b is a side elevational view of the preferred embodiment in accordance with the present invention in the closed position.

FIG. 7b is a side elevational view of the present invention illustrating the device 10 in the closed position, showing a generally symmetrical cavity 66 of the squeezing means 20 for compressing the male genital organ.

Figure 8:
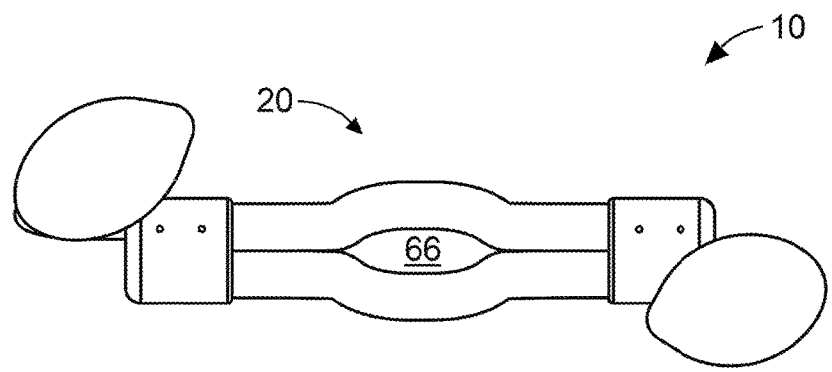
FIG. 8 is a top view of the present invention in the closed position.

FIG. 8 is a top view of the present invention in the closed position, showing the generally symmetrical cavity 66 of the squeezing means 20, for compressing the male genital organ, with the approximate dimensions of 1.5 inches wide and 0.4 inches of length.

Figure 9:
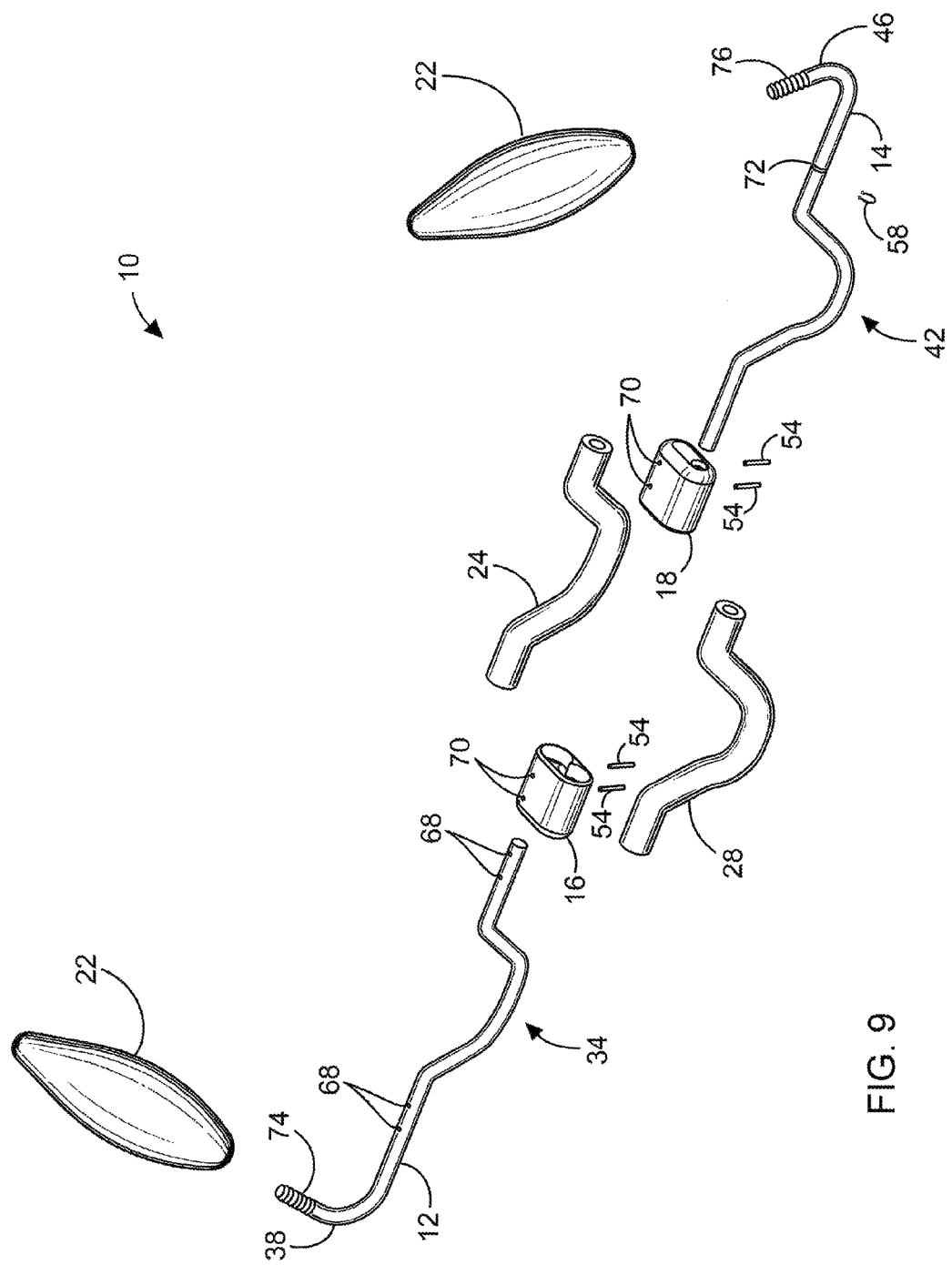
FIG. 9 is an exploded view of the preferred embodiment of the present invention.

FIG. 9 is an exploded view of the preferred embodiment in accordance with the present invention illustrating the device 10, showing the fixed member 12 comprising a plurality of pin holes 68 adapted to receive the plurality of spring pins 54. The first mounting bracket 16 and the second mounting bracket 18 include a plurality of pin holes 70 adapted to receive the plurality spring pins 54. The movable member 14 may include a groove 72 adapted to receive the retaining clip 58.

The handles 22 each handle securely attached, respectively, to the lever end 38 and 46 by suitable means, such as by mating threads. The lever end 38 and 46 may include, respectively, external threads 74 and 76. The handles 22 each may include inner threads (not shown) to engage, respectively, the external threads 74 and 76.

The first silicone sleeve 24 and the second silicone sleeve 28 may be mounted, respectively, on the V-shaped portion 34 and the V-shaped portion 42, by way of a tight fit for permanent attachment.

Figure 10:
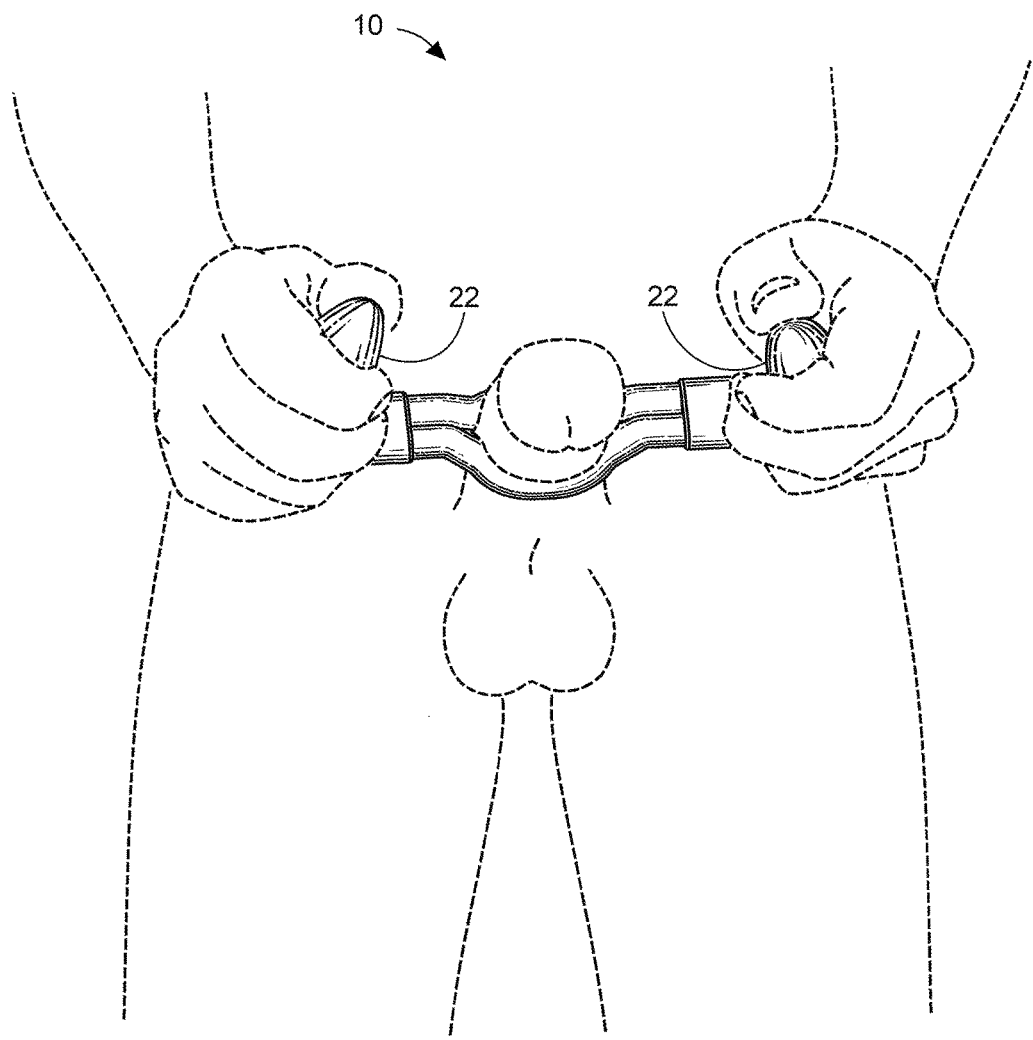
FIG. 10 shows the device according to FIG. 1 mounted on the male genital organ and being used by a consumer.

FIG. 10 is a perspective view of the preferred embodiment of the present invention, showing the device 10 according to FIG. 1 being used by a consumer. As configured, the handles 22 are adapted to facilitate an appropriate ergonomic positioning of a user's hands during exercise. The device 10 is adapted herein to provide the desired pressure and speed during the exercise eliminating hand fatigue, losing control, focus and motivation on the exercise. As configured, the device 10 facilitates the achievement of permanent size gains in length and gird to the male genital organ. The device 10 facilitates to achieve improved erections of the male genital organ.

Figure 11:
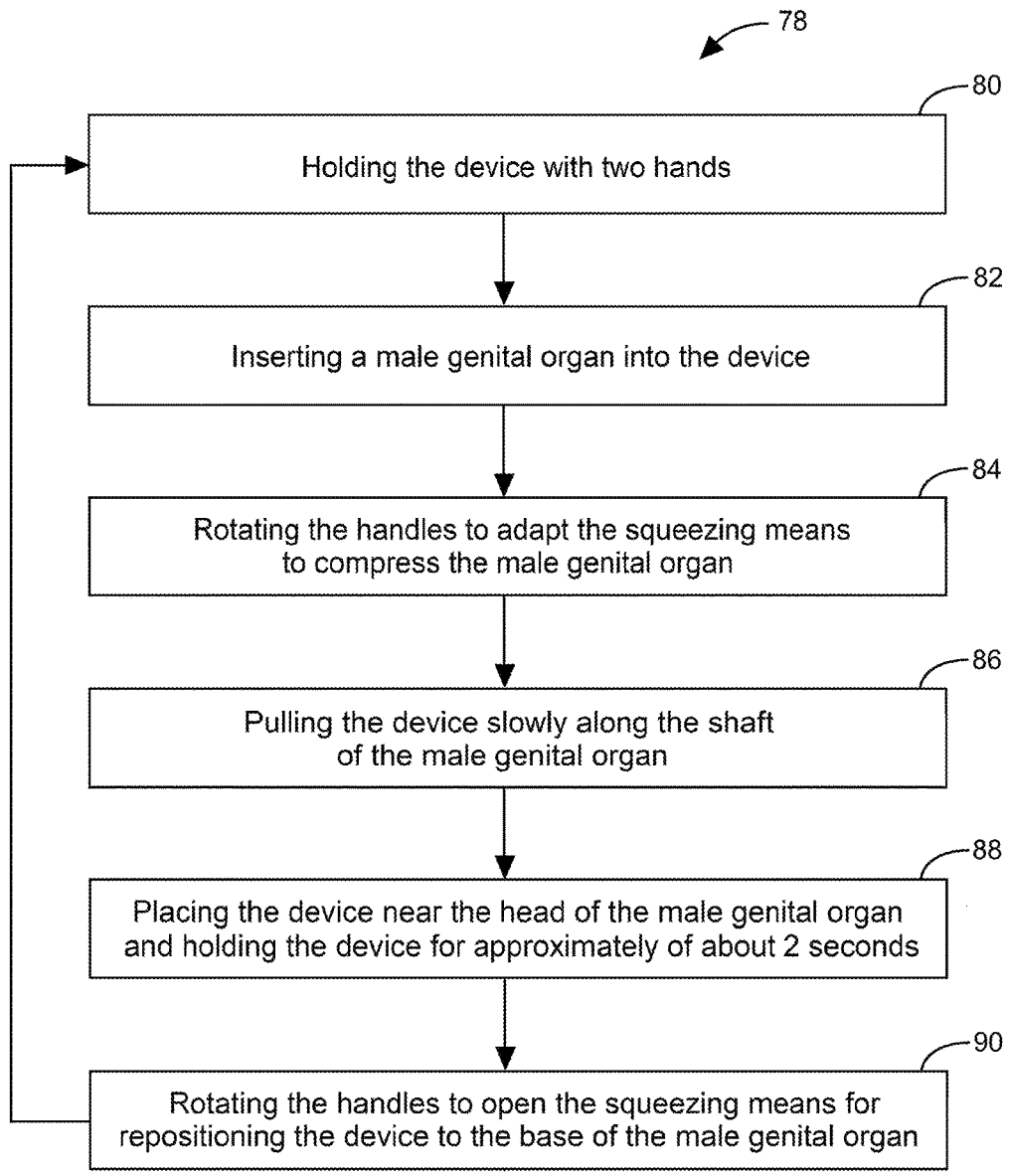
FIG. 11 is an operational flowchart, illustrating a method of operation of the device.

FIG. 11 is a flowchart showing a method of operation 78 of a device for exercising a male genital organ. Before initiating the process, the male genital organ needs to be warmed up; approximately of about 60% erect and lubricated. The process may be initiated as indicated at block 80 by way of holding the device with the user's hands, in the open position, parallel to the waist line. As indicated at block 82 the male genital organ can be inserted into the device. Next, as in block 84, the handles may be rotated to adapt the squeezing means to compress the base of the male genital organ. As indicated at block 86, the device may be slowly pulled along the shaft of the male genital organ to force the blood towards the head of the male genital organ. The device is placed near the head of the male genital organ as shown in block 88 and holding the device for approximately of about 2 seconds. The handles may be rotated to open the squeezing means as indicated at block 90 for repositioning the device to the base of the male genital organ.

While a particular form of the invention has been illustrated and described, it will be apparent that various modifications can be made without departing from the spirit and scope of the invention. For example, a device 10 may be made by variations in size, materials, shape and form. Accordingly, it is not intended that the invention be limited, except as by the appended claims.

What is claimed is:

1. An ergonomic two-hand operated device for exercising a male genital organ comprising:
    a fixed member, having a first cylindrical mounting portion, a V-shaped portion, a second cylindrical mounting portion and a lever end;
    a movable member, having a first cylindrical mounting portion, a V-shaped portion, a second cylindrical mounting portion and a lever end;
    a first mounting bracket having a through hole and a blind hole arranged in parallel;
    a second mounting bracket having a blind hole and a through hole arranged in parallel, said first mounting bracket and said second mounting bracket arranged to provide structural support for maintaining a spaced parallel relationship between said fixed member and said movable member;
    a pair of handles, each handle securely attached, respectively, with said lever end of the fixed member and with said lever end of the movable member, said handles adapted to facilitate an appropriate ergonomic positioning of a user's hands; and
    squeezing means, comprising a first silicone sleeve having a pair of sleeve end portions and a second silicone sleeve having a pair of sleeve end portions, said first silicone sleeve being mounted on said V-shaped portion of the fixed member and said second silicone sleeve being mounted on said V-shaped portion of the movable member wherein;
    the squeezing means is arranged to symmetrically compress and adapt to fit the shape of the male genital organ, said squeezing means is adapted to ensure the central positioning of the male genital organ during the exercise therein;

whereby the device is adapted to provide the desired pressure and speed during the exercise eliminating hand fatigue, losing control, focus and motivation on the exercise.

2. The device of claim 1 wherein said first cylindrical mounting portion and said second cylindrical mounting portion of said fixed member are securely attached, respectively, within said blind hole of said second mounting bracket and within said through hole of said first mounting bracket by way of a plurality of spring pins.

3. The device of claim 1 wherein said first cylindrical mounting portion and said second cylindrical mounting portion of said movable member are pivotally engaged, respectively, within said blind hole of said first mounting bracket and within said through hole of said second mounting bracket.

4. The device of claim 1 wherein said V-shaped portion of said fixed member and said V-shaped portion of said movable member each include an outwards curved shape.

5. The device of claim 4 wherein said outward curved shapes are designed to create a generally symmetrical cavity for compressing the male genital organ.

6. The device of claim 1 wherein said movable member includes a retaining clip.

7. The device of claim 6 wherein said retaining clip is arranged to maintain the alignment between each said V-shaped portions.

8. The device of claim 1 wherein said fixed member and said movable member are made from formed metal rod.

9. The device of claim 1 wherein the longitudinal axis of each said handles is lying at an inward angle from horizontal of approximately 75 degrees.

10. The device of claim 1 wherein said pair end portions of said first silicone sleeve arranged to maintain frictional contact with said pair end portions of said second silicone sleeve to ensure a sealed squeezing means around the male genital organ.

11. The device of claim 1 wherein said silicone sleeves are made of a single tubular piece of medical grade silicone.

12. The device of claim 1 wherein said blind holes and said through holes each include a counterbored section for overlapping said end portions of said silicone sleeves.

13. The device of claim 1 wherein said first silicone sleeve and said second silicone sleeve are mounted, respectively, on said V-shaped portion of said fixed member and said V-shaped portion of said movable member by way of tight fit for permanent attachment.

14. The device of claim 1 wherein said device is substantially free of pinch points to prevent the skin from being caught or injured between moving parts during the exercise.

15. A method of using a device for exercising a male genital organ for one user, the method comprising the steps of:
   a) holding the device with user's hands,
   b) inserting a male genital organ into the device;
   c) rotating handles to adapt the squeezing means to compress with the base of the male genital organ;
   d) pulling the device along the shaft until it reaches near the head of the male genital organ and then holding the device in place for approximately of about 2 seconds;
   e) rotating the handles to open the squeezing means for repositioning the device to the base of the male genital organ.

16. The method of claim 15 wherein the steps a) through e) are repeated.

* * * * *